(12) United States Patent
Hamasaki et al.

(10) Patent No.: US 9,005,445 B2
(45) Date of Patent: Apr. 14, 2015

(54) METHOD OF TESTING INTEGRITY OF MICROPOROUS MEMBRANE

(75) Inventors: Naoko Hamasaki, Tokyo (JP); Shoichi Ide, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 1099 days.

(21) Appl. No.: 12/530,065

(22) PCT Filed: Mar. 7, 2008

(86) PCT No.: PCT/JP2008/054147
§ 371 (c)(1),
(2), (4) Date: Sep. 4, 2009

(87) PCT Pub. No.: WO2008/111510
PCT Pub. Date: Sep. 18, 2008

(65) Prior Publication Data
US 2010/0096328 A1 Apr. 22, 2010

(30) Foreign Application Priority Data
Mar. 8, 2007 (JP) ................................ 2007-059053

(51) Int. Cl.
| | | |
|---|---|---|
| *B01D 65/10* | (2006.01) | |
| *B01D 69/02* | (2006.01) | |
| *B22F 9/24* | (2006.01) | |
| *B01J 13/00* | (2006.01) | |
| B01D 69/08 | (2006.01) | |
| G01N 15/08 | (2006.01) | |

(52) U.S. Cl.
CPC . *B22F 9/24* (2013.01); *B01D 69/08* (2013.01); *B01D 65/10* (2013.01); *B01D 65/102* (2013.01); *B01J 13/0043* (2013.01); *B22F 2998/00* (2013.01); *G01N 2015/084* (2013.01)

(58) Field of Classification Search
None
See application file for complete search history.

(56) References Cited

U.S. PATENT DOCUMENTS

| | | | | |
|---|---|---|---|---|
| 3,655,509 | A * | 4/1972 | Fields et al. | 435/239 |
| 3,770,625 | A * | 11/1973 | Wallis et al. | 210/694 |
| 2001/0051220 | A1* | 12/2001 | Ona et al. | 427/387 |
| 2005/0150831 | A1* | 7/2005 | Tabani et al. | 210/636 |
| 2006/0235085 | A1 | 10/2006 | Hongo et al. | |
| 2006/0257637 | A1* | 11/2006 | Pereira et al. | 428/221 |

FOREIGN PATENT DOCUMENTS

| | | |
|---|---|---|
| CN | 1297427 A | 5/2001 |
| CN | 1871086 A | 11/2006 |
| EP | 1647345 | 4/2006 |
| JP | 7-132215 | 5/1995 |
| JP | 3328857 | 5/1995 |
| JP | 2902954 | 4/1996 |
| JP | 2005-40756 | 2/2005 |
| JP | 2006-55784 | 3/2006 |
| WO | 99/36376 | 7/1999 |
| WO | 2005/007328 | 1/2005 |

OTHER PUBLICATIONS

Chinese Office Action issued with respect to Chinese Patent Application No. 200880007373.4, dated Feb. 23, 2011.
Gitis et al., "Nanoscale probes for the evaluation of the integrity of ultrafiltration membranes" *Journal of Membrane Science*, vol. 276, No. 1-2, pp. 199-207, published online Nov. 17, 2005.
European Search Report issued with respect to patent family member European Patent Application No. 08721565.3, dated Mar. 3, 2011.
Saori Hanada, "Integrity Test-yo Colloid Ryushi no Chosei", Heisei 18 Nendo The Society of Fiber Science and Technology, Japan Nenji, Taikai Yokoshu, p. 165, along with an English language Translation, Jun. 12, 2006.
International Search Report for PCT/JP2008/054147, mailed Jun. 10, 2008.
International Preliminary Report on Patentability for PCT/JP2008/054147, issued Sep. 29, 2009.
Machine translation of JP 8-89788 (corresponding to JP 2902954), Apr. 9, 1996.
Machine translation of JP 7-132215 (corresponding to JP 3328857), May 23, 1995.

* cited by examiner

*Primary Examiner* — Katherine Zalasky
(74) *Attorney, Agent, or Firm* — Greenblum & Bernstein, P.L.C.

(57) ABSTRACT

The present invention provides a method of testing the integrity of a microporous membrane using a colloid solution containing metal particles or metal compound particles that can accurately determine the integrity of a virus removal membrane formed of hydrophilized synthetic polymer that has been subjected to protein solution filtration, and to provide a method of producing the colloid solution. The colloid solution comprises a solvent and metal particles dispersed in the solvent, and the solvent comprises components (A) and (B), (A) and (C), or (A), (B), and (C), wherein the component (A) is an anionic polymer having a sulfonic acid group, the component (B) is at least one nonionic surfactant selected from the group consisting of a nonionic surfactant having a polycyclic structure in a hydrophobic moiety and a polyoxyethylene sorbitan fatty acid ester, and the component (C) is a water-soluble polymer having a pyrrolidone group.

18 Claims, No Drawings

US 9,005,445 B2

METHOD OF TESTING INTEGRITY OF MICROPOROUS MEMBRANE

TECHNICAL FIELD

The present invention relates to a method of testing the integrity of a membrane using a colloid solution containing metal particles.

BACKGROUND ART

Metal particles having an average particle diameter of 1 to 100 nm have been used for an integrity test conducted on a virus removal membrane formed of regenerated cellulose as viral substitute particles. There is a good correlation between removal of viruses and removal of gold particles used as substitute particles (see Patent Document 1). A metal or metal compound colloid solution that contains a water-soluble polymer dispersant having a nitrogen-containing group and is used for an integrity test conducted on a virus removal membrane formed of a synthetic polymer such as hydrophilized polyvinylidene fluoride and the like has been proposed (see Patent Document 2). A gold colloid solution that contains a nonionic surfactant has been proposed as a stable colloid solution, although the solution is not used for an integrity test conducted on a virus removal membrane (see Patent Document 3).

It is preferable to have a step of washing a membrane that has been used as a virus removal membrane in a practical integrity test to thereby reduce the amount of residue in the membrane as much as possible. A method of washing a synthetic membrane after use comprising using citric acid has been proposed (see Patent Documents 2 and 4). However, when using the metal or metal compound colloid solution disclosed in Patent Document 2, the integrity of a virus removal membrane that comprises a hydrophilized synthetic polymer and has been subjected to protein filtration and washing cannot necessarily be accurately tested.

Specifically, proteins and the like that remain after washing the virus removal membrane that comprises a hydrophilized synthetic polymer interact with the colloid solution disclosed in Patent Document 2 (i.e., there has been arisen a problem that proteins and the like that remain in the virus removal membrane adhere to the colloid).

[Patent Document 1] Japanese Patent No. 3328857
[Patent Document 2] WO 2005/007328
[Patent Document 3] Japanese Patent No. 2902954
[Patent Document 4] JP-A-2006-55784

DISCLOSURE OF THE INVENTION

Problems to be Solved by the Invention

An object of the present invention is to solve the above problem, and provide a method of testing the integrity of a microporous membrane using a colloid solution containing metal particles that can accurately determine the integrities of both cellulose virus removal membrane and hydrophilized synthetic polymer virus removal membrane after filtrating protein solution.

Means for Solving the Problems

The inventors of the present invention conducted extensive studies in order to achieve the above object. As a result, the inventors have found that by adding an anionic polymer having a sulfonic acid group to a colloid solution that contains a nonionic surfactant selected from of either a nonionic surfactant having a polycyclic structure in a hydrophobic moiety or a polyoxyethylene sorbitan fatty acid ester and/or a water-soluble polymer dispersant having a pyrrolidone group and metal particles or metal compound particles, an accurate integrity test (i.e. the difference in logarithmic reduction value (LRV) of metal particle or metal compound particle is within 0.1 in comparison with a blank test) can be conducted surprisingly, even though the membrane is a hydrophilized synthetic polymer virus removal membrane which is washed after filtrating protein.

The inventors also found that a hydrophilized synthetic polymer membrane can be washed without damaging the hydrophilic moiety and the effects affecting the measurement due to proteins remaining in the membrane can be reduced as much as possible by combining a washing method of utilizing a basic buffer or a mixed solution of sodium hypochlorite and a nonionic surfactant having a polycyclic structure in a hydrophobic moiety as a washing agent so that the accurate integrity test can be done.

Specifically, the present invention is as follows.

(1) A method of testing the integrity of a microporous membrane comprising filtering a colloid solution through the microporous membrane, the colloid solution comprising a solvent and metal particles dispersed in the solvent, and the solvent comprising components (A) and (B), (A) and (C), or (A), (B) and (C), wherein the component (A) is an anionic polymer having a sulfonic acid group; the component (B) is at least one nonionic surfactant selected from the group consisting of a nonionic surfactant having a polycyclic structure in a hydrophobic moiety and a polyoxyethylene sorbitan fatty acid ester, and the component (C) is a water-soluble polymer having a pyrrolidone group.

(2) The method according to (1), wherein the microporous membrane is a synthetic polymer virus removal membrane or a cellulose virus removal membrane.

(3) The method according to (2), wherein the synthetic polymer virus removal membrane is a hydrophilized thermoplastic polymer membrane.

(4) The method according to (3), wherein the thermoplastic polymer of the hydrophilized thermoplastic polymer membrane is selected from the group consisting of polyvinylidene fluoride, polyethersulfone, and polysulfone.

(5) The method according to (1), wherein the metal of the metal particles is selected from the group consisting of gold, silver, platinum, rhodium, palladium, ruthenium, iridium, osmium, iron, and copper.

(6) The method according to (5), wherein the metal particles have an average particle diameter of 10 to 50 nm.

(7) The method according to (6), wherein the coefficient of variation of the average particle diameter of the metal particles is 27% or less.

(8) The method according to (1), wherein the anionic polymer having a sulfonic acid group is a polystyrene sulfonate.

(9) The method according to (1), wherein the nonionic surfactant having a polycyclic structure in a hydrophobic moiety is at least one compound selected from the group consisting of a polyoxyethylene polycyclic phenyl ether, polyoxyethylene β-naphthyl ether, and polyoxyethylene styryl phenyl ether.

(10) The method according to (1), wherein the polyoxyethylene sorbitan fatty acid ester is polyoxyethylene sorbitan monolaurate and/or polyoxyethylene sorbitan monooleate.

(11) The method according to (1), wherein the water-soluble polymer having a pyrrolidone group is polyvinylpyrrolidone or a polyvinylpyrrolidone/styrene copolymer.

(12) The method according to (1), wherein the virus removal membrane is a membrane which has been washed with a basic buffer after filtrating protein solution.

(13) The method according to (12), wherein the basic buffer is selected from the group consisting of a carbonate, a bicarbonate, a borate, and a phosphate.

(14) The method according to (1), wherein the virus removal membrane is a membrane which has been washed with a mixed solution that contains a nonionic surfactant having a polycyclic structure in a hydrophobic moiety and sodium hypochlorite after filtrating protein solution.

(15) The method according to (1), wherein the metal colloid solution is obtained by dissolving the component (B) and/or the component (C) in a solution prepared by dissolving a metal compound in a solvent to precipitate metal particles, and then further dissolving the component (A) in the solution.

Effects of the Invention

It become possible to conduct the accurate integrity test for a hydrophilized synthetic polymer virus removal membrane after filtrating a protein solution by utilizing the method of testing the integrity of a microporous membrane using the colloid solution containing metal particles according to the present invention.

BEST MODE FOR CARRYING OUT THE INVENTION

The method of testing the integrity of a microporous membrane using a colloid solution according to the present invention and a method of preparing the metal colloid solution are described in detail below.

The metal particles contained in the colloid solution used for the integrity test according to the present invention refer to particles formed of a metal element or a metal compound such as a metal oxide. The metal that forms the metal particles or the metal compound particles contained in the colloid solution is not particularly limited insofar as metal particles or metal compound particles having a particle diameter of 1 to 100 nm can be formed in a solvent, and preferably does not undergo a chemical reaction in the colloid solution used for the integrity test. The metal is preferably gold, silver, rhodium, palladium, ruthenium, iridium, osmium, iron, or copper. Among these, gold, silver, and copper are preferable, with gold being most preferable.

The metal particles selves contained in the colloid solution used for the integrity test according to the present invention do not undergo a chemical reaction. This means that in the solvent the metal particles do not bond, decompose, or deform by chemically reacting with other metal particles each other and/or the metal particles do not chemically reacted with a porous body or a microporous membrane.

In order to use the colloid solution for the integrity test conducted on a porous membrane, it is preferable that the colloid solution can be identified using visible light. It is preferable that the colloid solution have its maximum absorption in the visible wavelength region. The term "visible wavelength region" refers to a wavelength range from 360 to 830 nm. For example, when using gold as the metal that forms the metal particles or metal compound particles, the color of the colloid solution is purplish red to purple (maximum absorption wavelength: 500 to 600 nm), although the color of the colloid solution differs depending on the particle diameter.

The integrity test according to the present invention is conducted to confirm the performance of a virus removal membrane that removes viruses from a solution that contains proteins, physiologically active substances, and the like after use. The integrity test may be conducted in various ways. A method of filtering metal particles as viral substitute particles has high reliability since the principle is the sieve filtration of particles in the same manner as virus removal so that a correlation between characteristic values based on an identical mechanism can be obtained. Moreover, according to the method of filtering a colloid solution, the colloid solution can be easily prepared, and the concentration of the colloid solution can be easily and accurately measured. When conducting the integrity test, it is preferable to wash the membrane before filtering the colloid solution to remove proteins, lipids, and the like that remain in the membrane to the utmost extent so that a change in pore size distribution due to clogging or the like can be reduced as much as possible.

The particle diameter of the metal particles used in the present invention should be 1 to 100 nm in order to maintain a stable dispersion state. The particle diameter of the metal particles used in the present invention is preferably 1 to 50 nm. The lower limit of the particle diameter of the metal particles must be 1 nm or more when the metal particles are used for the integrity test conducted for a virus removal membrane. The lower limit of the particle diameter of the metal particles is preferably 5 nm or more, more preferably 10 nm or more, and particularly preferably 15 nm or more. The upper limit of the particle diameter of the metal particles must be 100 nm or less in order to maintain a stable dispersion state. The upper limit of the particle diameter of the metal particles is preferably 75 nm or less, more preferably 50 nm or less, and particularly preferably 45 nm or less. The particle diameter of the metal particles used herein is normally expressed by the circle equivalent diameter. Specifically, the projection area of the particle is calculated from photograph observed through an electron micrograph, and the particle diameter of the metal particle is expressed by the diameter of a circle having an area equal to the projection area. The average particle diameter refers to the number average circle equivalent diameter.

When testing the integrity of a virus removal membrane that aims to remove small viruses (e.g., parvovirus) having a diameter of 20 to 25 nm, the average particle diameter of the metal particles is preferably 15 to 25 nm. The removal rate of the metal particles when filtering a colloid solution having an average particle diameter of 15 to 25 nm through a virus removal membrane that is used to remove small viruses has a high correlation with the removal rate of small viruses (e.g., parvovirus).

The coefficient of variation of the particle diameter of the metal particles used in the present invention is preferably 30% or less when the metal particles are used for the integrity test conducted on a virus removal membrane. The coefficient of variation of the particle diameter of the metal particles is more preferably 27% or less. The coefficient of variation is calculated by the following expression (1).

$$\text{Coefficient of variation (\%)} = \sigma \text{ (standard deviation of particle diameter)} \times 100 / \text{average particle diameter} \quad (1)$$

It is preferable that the metal particles used in the present invention have an almost isotropic shape when the metal particles are used for the integrity test conducted on a porous membrane. The expression "particle has an almost isotropic shape" here refers to the case where the ratio of the major axis to the minor axis of the particle is 1 to 2, preferably 1.0 to 1.8.

The content of the metal particles used in the present invention is preferably 1 to 1000 ppm, more preferably 10 to 800 ppm, and still more preferably 20 to 700 ppm. If the content of the metal particles exceeds 1000 ppm, the dispersion stability of the metal particles may deteriorate. If the content of the metal particles is less than 1 ppm, usability, as the use for the integrity test, may be impaired. The content of the metal particles is preferably 0.0001 to 0.1 wt %, more preferably 0.001 to 0.08 wt %, and still more preferably 0.002 to 0.07 wt % when expressed in the unit "wt %".

In order to use the colloid solution for the integrity test conducted on a microporous membrane, it is preferable that the colloid solution contain only one type of metal particles. The metal particles allow accurate identification and quantitative determination, do not undergo a chemical reaction with other metal particles, and/or do not undergo a chemical reaction with a porous body or a microporous membrane. If the colloid solution contains several types of metal particles, an accurate measurement may not be performed due to the difference in absorption spectrum or the like. Since the particle diameter and the coefficient of variation of metal particle can be easily controlled by adjusting the reaction conditions, particles having almost the same size as that of the target virus particles can be produced. It is difficult to stably produce plural types of metal particles to have an identical particle diameter.

The anionic polymer having a sulfonic acid group used in the present invention is preferably at least one polymer selected from polystyrene sulfonic acid, salts thereof, an alkylated hydroxyethyl cellulose sulfonate, polyvinyl sulfate, dextran sulfate, salts thereof, and the like. Any salts can be used, examples of the salts include commercially available sodium salts and potassium salts. The density of sulfonic acid groups in the molecule is not particularly limited insofar as the dispersion stability of the particles and the solubility of the polymer are not affected. It is preferable that the anionic polymer contain 300 to 400 sulfonic acid groups per unit molecular weight (i.e., 70,000) of the anionic polymer. The anionic polymer may contain a functional group other than the sulfonic acid group in the molecule, though not specifically limited to, insofar as the dispersion stability of the particles is not affected. It is undesirable that the anionic polymer contain a carboxyl group from the viewpoint of interaction with residual proteins. The anionic polymer having a sulfonic acid group directly acts and encompasses the metal particles and prevents aggregation so that the metal particles exhibit dispersibility (protective colloid effects). The protective colloid effects include preventing aggregation of the metal particles, maintaining a constant surface potential, and suppressing adhesion of the metal particles to other materials. Since the hydrophilic group of the polymer has anionic properties, the surface of the particles is charged to a larger extent so that there is an effect that increases the electric double layer repulsive force between the surface of the particles and a material which has the same amounts of charge. Furthermore, there is another effect that suppresses hydrophobic interaction with an amino group of an amino acid that forms a protein, since the anionic polymer having a sulfonic acid group exhibits high hydrophilicity as compared with an anionic polymer having other hydrophilic groups (e.g., carboxylic acid group).

The molecular weight of the anionic polymer having a sulfonic acid group used in the present invention is preferably $1 \times 10^3$ to $2 \times 10^6$, more preferably $2 \times 10^3$ to $1 \times 10^6$, still more preferably $5 \times 10^3$ to $5 \times 10^5$, and most preferably $7 \times 10^3$ to $1 \times 10^5$. If the molecular weight of the anionic polymer having a sulfonic acid group is $1 \times 10^3$ or less, the dispersion stability of the colloid may deteriorate. If the molecular weight of the anionic polymer having a sulfonic acid group is $2 \times 10^6$ or more, it may be unpreferable from the viewpoint of difficulty to affect the viscosity, solubility into a solvent, handling capability, and the particle size of the colloid.

The content of the anionic polymer having a sulfonic acid group in the colloid solution according to the present invention is preferably 0.01 to 20 wt %, more preferably 0.05 to 10 wt %, and still more preferably 0.1 to 5 wt %. If the content of the anionic polymer having a sulfonic acid group is less than 0.01 wt %, interaction with a synthetic polymer microporous membrane may unpreferably not be suppressed. If the content of the anionic polymer having a sulfonic acid group is more than 20 wt %, the dispersion stability of the particles may unpreferably deteriorate.

The colloid solution according to the present invention is characterized in that a nonionic surfactant of either a nonionic surfactant having a polycyclic structure in a hydrophobic moiety or a polyoxyethylene sorbitan fatty acid ester, and/or a water-soluble polymer having a pyrrolidone group are/is used in combination with the anionic polymer having a sulfonic acid group. Using these two or three additives in combination, there are added effects that further improves the dispersion stability of the metal particles, and suppress adhesion of the metal particles to proteins that remain in the membrane, for example.

The nonionic surfactant having a polycyclic structure in a hydrophobic moiety used in the present invention refers to a nonionic surfactant having two or more ring structures or a carbon condensed ring. The nonionic surfactant having a polycyclic structure in a hydrophobic moiety is preferably a polyoxyethylene polycyclic phenyl ether, polyoxyethylene β-naphthyl ether, or polyoxyethylene styryl phenyl ether. Hydrophobicity of the nonionic surfactant becomes low due to a polycyclic structure in a hydrophobic moiety so that interaction with a hydrophobic moiety of a synthetic polymer microporous membrane is effectively suppressed. A nonionic surfactant having a polycyclic structure is known to form a large micelle. A large micelle formed by the nonionic surfactant having a polycyclic structure adheres to the side chain of the anionic polymer having a sulfonic acid group due to hydrophobic interaction so that interaction with an amino group of an amino acid that forms a protein is sterically limited.

The polyoxyethylene sorbitan fatty acid ester used in the present invention refers to a nonionic surfactant having a structure in which the hydrophilic moiety has an oxyethylene chain and a polyhydric alcohol and a fatty acid are ester-bonded on the side chain. The polyoxyethylene sorbitan fatty acid ester also has the same effects as those of the nonionic surfactant having a polycyclic structure.

The water-soluble polymer having a pyrrolidone group used in the present invention is preferably polyvinylpyrrolidone or an N-vinylpyrrolidone/styrene copolymer. The water-soluble polymer having a pyrrolidone group directly adheres to colloid and encompasses the metal particles to prevent aggregation so that the dispersibility of the metal particles is exhibited, that is, the water-soluble polymer has so-called "protective colloid effect." In particular, a polymer that is charged in a different polarity to that of the metal particles more strongly adheres to the surface of the metal particles due to a static electricity effect, and is stable even if a change in state (temperature or salt concentration) of the solution occurs.

The molecular weight of the water-soluble polymer having a pyrrolidone group used in the present invention is preferably $1 \times 10^3$ to $2 \times 10^6$, more preferably $2 \times 10^3$ to $1 \times 10^6$, still more preferably $5 \times 10^3$ to $1 \times 10^5$, and most preferably $7 \times 10^3$ to $5 \times 10^4$. If the molecular weight of the water-soluble polymer having a pyrrolidone group is less than $1 \times 10^3$, the dispersion stability of the colloid may unpreferably deteriorate. If the molecular weight of the water-soluble polymer having a pyrrolidone group is more than 2×10⁶, it may be unpreferable from the viewpoint of difficulty to affect the viscosity, solubility into a solvent, handling capability, and the particle size of the colloid.

The content of the nonionic surfactant of either the nonionic surfactant having a polycyclic structure in a hydrophobic moiety or the polyoxyethylene sorbitan fatty acid ester and/or the water-soluble polymer having a pyrrolidone group according to the present invention is preferably 0.001 to 10 wt %, more preferably to 0.01 to 5 wt %, and more preferably 0.05 to 3 wt %. If the content of the nonionic surfactant of either the nonionic surfactant having a polycyclic structure in a hydrophobic moiety or the polyoxyethylene sorbitan fatty acid ester and/or the water-soluble polymer having a pyrrolidone group is less than 0.001 wt %, dispersion stability may unpreferably deteriorate. Note that the upper limit of the above content is not particularly limited insofar as solubility in a solvent and the like are not adversely affected.

The colloid solution according to the present invention may be prepared by dissolving a metal compound as raw material in a solvent, and reducing to the metal. As the metal compound (raw material), chloroauric acid, silver nitrate, chloroplatinic acid, rhodium (III) chloride, palladium (II) chloride, ruthenium (III) chloride, chloroiridate, osmium (VII) oxide, or the like may be used. Examples of a reducing agent include citric acid, sodium citrate, tannic acid, hydrazine, sodium borohydride, and the like. The reaction temperature may be in the range from room temperature to the boiling point of the solvent, and preferably from 40° C. to the boiling point of the solvent. The reaction time is from several minutes to several days. The colloid solution according to the present invention may be obtained by adding a given amount of the nonionic surfactant of either the nonionic surfactant having a polycyclic structure in a hydrophobic moiety or the polyoxyethylene sorbitan fatty acid ester and/or the water-soluble polymer having a pyrrolidone group to the solution after the reduction reaction, and further adding a given amount of the anionic polymer having a sulfonic acid group to the mixture.

A method of producing the colloid solution containing metal compound particles according to the present invention is not particularly limited. For example, a method of obtaining particles such as metal oxide particles or metal hydroxide condensate particles by subjecting a metal chloride, that is a metal inorganic salt (e.g., nitrate or sulfate), or a metal organic salt (e.g., oxalate or acetate) to alkali hydrolysis, thermal hydrolysis, ion exchange, or the like may be used. A high temperature condition and pressurized condition also may be used to complete the reaction promptly.

As the solvent used for the metal compound (raw material) and the dispersion solvent used for the colloid solution according to the present invention, water, a water-soluble organic solvent, or a mixture thereof may be used in general. Examples of the water-soluble organic solvent include ethanol, methanol, ethylene glycol, and the like. Water, ethanol, methanol, or a mixture thereof is preferably used. Among these, water is most preferable.

Examples of the material for the microporous membrane used in the present invention include cellulose and a synthetic polymer. As the cellulose, regenerated cellulose, natural cellulose, or cellulose acetate is preferably used.

The synthetic polymer used in the present invention is a thermoplastic polymer, and polyvinylidene fluoride, polyethersulfone, or polysulfone is preferably used. Since polyvinylidene fluoride, polyethersulfone, and polysulfone are hydrophobic, it is preferable to be subjected to hydrophilization when these materials are used for a virus removal membrane. The term "hydrophilization" used herein refers to hydrophilizing the surface of the membrane or the surface of the pores. A hydrophilization treatment may be performed according to a known method such as grafting, coating, or crosslinking. The term "hydrophilic" used herein means that the membrane has high water wettability. The hydrophilization method is not particularly limited. For Example, a method that the microporous membrane is immersed in a solution containing a surfactant, and dried so that the surfactant remains in the microporous membrane, a method of grafting the pore surface of the microporous membrane with a hydrophilic acrylic monomer, methacrylic monomer or the like by applying radiation such as electron beams or γ-rays or using a peroxide, a method of previously mixing a hydrophilic polymer during membrane formation, a method of immersing the microporous membrane in a solution containing a hydrophilic polymer, and drying the microporous membrane so that the pore surface of the microporous membrane is coated with a film of the hydrophilic polymer, and the like can be given.

The pressure applied when filtering the colloid solution according to the present invention through a virus removal membrane is not particularly limited insofar as the structure of the microporous membrane is not affected. When using a cellulose membrane that exhibits low pressure resistance, the pressure applied during filtration is preferably 1 to 100 kPa, and more preferably 20 to 80 kPa. When using a membrane formed of polyvinylidene fluoride, polyethersulfone, or polysulfone, high pressure filtration can be possible, and thus it is preferable to apply a pressure as high as possible during filtration. In this case, the pressure applied is preferably 100 to 600 kPa, and more preferably 100 to 300 kPa.

The concentration of the colloid solution is measured by the following method. The absorption spectrum of the colloid solution is measured using a spectrophotometer or the like to determine the maximum absorption wavelength. The absorbance of the colloid solution at the maximum absorption wavelength is measured before and after filtration. The removal rate of the colloid is expressed by the logarithmic reduction value (LRV). Assuming that the absorbance before filtration is Co and the absorbance after filtration is Cf, the logarithmic reduction value is calculated by the following expression (2).

$$\text{Logarithmic reduction value (LRV)} = \text{Log}_{10}(Co/Cf) \tag{2}$$

In the present invention, the integrity test of the membrane can be accurately conducted when the metal particles adhere to the membrane material to only a small extent. If the metal particles adhere to the membrane material to only a small extent, the performance of the membrane can be evaluated by utilizing a particle sieving principle based on the size of the pores in the membrane. The degree of adhesion of the metal particles to the membrane material may be determined based on the dependence of the LRV of the metal particles on a change in the size of the metal particles. Because, a correlation between the size of the metal particles and the removal value is not observed when the metal particles adhere to the membrane material. The present invention adopts a method of measuring the LRV of the metal particles using a porous membrane (blank filter) before use as a virus removal membrane using metal particles having a particle diameter that is almost the same as the average pore size determined by the water flow method of the filter while changing only the additive, as a method of determining the degree of adhesion with ease. The additive is used here to prevent the metal particles from adhering to the porous membrane, i.e., the metal particles adhere to the porous membrane to a large extent when the additive is not added. Since the metal particle removal test for the integrity test is based on the removal value due to the size of the metal particles, the effects of adhesion must be prevented. When the metal particles strongly adhere to the surface of the membrane, the LRV of the metal particles is equal to or less than the detection limit (LRV>3.0) regardless of the amount of filtration. In the present invention, whether the integrity of the blank filter can be accurately measured or not may be determined by confirming a phenomenon in which the LRV of a solution filtered at a rate of 0.5 to 2.5 l/m² is smaller than 2.0 and the particle capture capability of the membrane decreases, i.e. the LRV decreases, as the amount of filtration increases, for example.

In the present invention, whether the integrity of a virus removal membrane can be accurately measured after using as a virus removal membrane or not may be determined by measuring the LRV of the metal particles using the virus removal membrane that has been subjected to filtration of protein aqueous solution for a given period of time and then subjected to washing. Specifically, before and after the microporous membrane is used as a virus removal membrane, a colloid solution having a same average particle diameter is filtered through a microporous membrane having a same average pore diameter by a method of filtrating under same conditions. It is determined that the metal particles adhere to residual proteins and the membrane material after washing to only a small extent if the difference in LRVs (measured values) is small. If the metal particles adhere to only a small extent, the performance of the membrane can be evaluated by utilizing a particle sieving principle based on the size of the pores in the membrane after the membrane has been used as a virus removal membrane. Therefore, the method can be suitably used for the integrity test of the practical virus removal membrane. In the present invention, the integrity test can be accurately conducted after using as the virus removal membrane, if the difference in LRV of the metal particles measured before and after using as the virus removal membrane is 0.1 or less, for example.

The basic buffer used in the present invention is a buffer solution prepared by mixing a carbonate, a bicarbonate, a borate, a phosphate, and the like in combination so that the buffer has a pH of about 10. Any type of the salts may be used, commercially available sodium salts and potassium salts can be given. Residues in the synthetic polymer membrane can be flowed out from the membrane without damaging the hydrophilic moiety of the membrane by utilizing the basic buffer as a washing solution.

The mixed solution that contains a nonionic surfactant having a polycyclic structure in a hydrophobic moiety and sodium hypochlorite used to wash the membrane in the present invention refers to a mixed solution of a nonionic surfactant having two or more phenyl groups or a carbon condensed ring and sodium hypochlorite. As the mixed solution that contains the nonionic surfactant having a polycyclic structure in a hydrophobic moiety and sodium hypochlorite, a mixed solution of sodium hypochlorite and a nonionic surfactant having a polycyclic structure in a hydrophobic moiety such as a polyoxyethylene polycyclic phenyl ether, polyoxyethylene β-naphthyl ether, polyoxyethylene styryl phenyl ether or the like is preferable. The mixed solution has an effect that residues in the membrane are solubilized into a washing solvent so that the residues are flowed out from the membrane.

The washing method according to the present invention is not particularly limited insofar as it is a common washing method. For example, a washing method that causes the washing solution to flow through the microporous membrane in the same direction as the organic substance filtration direction (hereinafter referred to as "forward washing"), a washing method that causes the washing solution to flow through the microporous membrane in the direction opposite to the organic substance filtration direction (hereinafter referred to as "back washing"), or the like may be given.

The washing temperature is not particularly limited insofar as the washing solution is not affected, but is preferably 4 to 40° C.

The washing pressure is not particularly limited insofar as the structure of the microporous membrane is not affected. When using a cellulose membrane having low pressure resistance, the washing pressure is preferably 1 to 100 kPa, and more preferably 20 to 80 kPa. When using a polyvinylidene fluoride membrane, polyethersulfone membrane, or polysulfone membrane having high pressure resistance, it is preferable to use the washing pressure as high as possible. In this case, the washing pressure is preferably 100 to 600 kPa, and more preferably 100 to 300 kPa.

The present invention is further concretely described below by way of examples and comparative examples.

Example 1

Preparation of Colloid Solution

A reaction vessel was charged with 80 g of an aqueous solution of 14.7 mM chloroauric acid (special grade, manufactured by Wako Pure Chemical Industries, Ltd.). 320 g of distilled water and 18 g of a 4% sodium citrate aqueous solution were added to the solution, and the mixture was reacted at 76° C. for 30 minutes. After completion of the reaction, the mixture was cooled in a water bath for 15 minutes. After the addition of 6.7 g of polyoxyethylene β-naphthyl ether ("Solsperse (registered trademark) 27000" manufactured by Lubrizol Japan Ltd.) as a nonionic surfactant having a polycyclic structure in a hydrophobic moiety, 8.3 g of a 10% aqueous solution of poly(sodium 4-styrenesulfonate) (PSSA-Na, molecular weight: 70,000, manufactured by Sigma-Aldrich, Inc.) was added to the mixture to obtain a purple-red gold colloid solution. 10 g of the reaction solution was ten-fold diluted with an aqueous solution prepared by adding 1.6 g of a solution of Solsperse (registered trademark) 27000 and 2.0 g of a 10% aqueous solution of PSSA-Na (molecular weight: 70,000) to 96.4 g of water for injection to obtain a red diluted gold colloid solution. The absorption spectrum was measured using a spectrophotometer. The maximum absorption was observed at 529 nm (attributed to the plasmon absorption of gold). The gold colloid solution was dried on a mesh with a collodion membrane, and observed using a transmission electron microscope. The gold particles were sufficiently dispersed, and had an average particle diameter of 22.3 nm.

<Production of Filter>

A composition containing 49 wt % of a polyvinylidene fluoride resin ("Sofef 1012", crystalline melting point: 173° C., manufactured by Solvay S.A.) and 51 wt % of dicyclohexyl phthalate (Industrial grade, manufactured by Osaka Organic Chemical Industry Ltd.) was mixed at 70° C. using a Henschel mixer, and cooled to obtain a powder. The powder was charged in a twin-screw extruder ("Labo Plastomill Model 50C150" manufactured by Toyo Seiki Seisaku-Sho, Ltd.) from a hopper, and was subjected to melt-mixing at 210° C. to uniformly melt. The molten was extruded in a form of hollow fiber from a spinning nozzle formed of a circular orifice having an inner diameter of 0.8 mm and outer diameter of 1.1 mm at a discharge speed of 17 m/min while causing dibutyl phthalate (manufactured by Sanken Kako Co., Ltd.)

with a temperature of 130° C. to flow inside the hollow portion at a flow rate of 8 ml/min. The extruded product was cooled and solidified in a water bath maintained at 40° C., and wound in a skein at 60 m/min. After that, dicyclohexyl phthalate and dibutyl phthalate were extracted and removed using 99% methanol-modified ethanol (manufactured by Imazu Chemical Co., Ltd.), and ethanol adhering to the membrane was replaced with water. The membrane was immersed in water and in this situation heated at 125° C. for one hour using a high-pressure steam sterilizer ("HV-85" manufactured by Hirayama Manufacturing Corporation). After that, water adhering to the membrane was replaced with ethanol, and the membrane was then dried at 60° C. in an oven to obtain a hollow fiber microporous membrane. Note that the extraction step to the drying step were carried out while securing the membrane at a constant length in order to prevent shrinkage.

The microporous membrane was then subjected to a hydrophilization treatment according to a grafting method. A solution obtained by dissolving hydroxypropyl acrylate (reagent grade, manufactured by Tokyo Kasei Kogyo Co., Ltd.) in a 25 vol % aqueous solution of 3-butanol (special grade, manufactured by Junsei Kagaku Co., Ltd.) so that the hydroxypropyl acrylate content was 8 vol %, and bubbling nitrogen through the solution at 40° C. for 20 minutes was used as a reaction liquid. The microporous membrane was irradiated with γ-rays (dose: 100 kGy) from $Co^{60}$ (irradiation source) in a nitrogen atmosphere while cooling the microporous membrane to −60° C. with dry ice. After irradiation, the membrane was allowed to stand for 15 minutes under reduced pressure equal to or less than 13.4 Pa, caused to come in contact with the above reaction liquid at 40° C., and allowed to stand for one hour. After washing the membrane with ethanol, the membrane was dried at 60° C. for four hours under vacuum to obtain a microporous membrane. The average pore size determined by the water flow method of the obtained membrane was 23.1 nm. A filter (membrane area: 0.001 $m^2$) was produced using the virus removal porous hollow fiber membrane formed of hydrophilized polyvinylidene fluoride (PVDF) thus obtained.

<Integrity Test>

A protein aqueous solution prepared by diluting a human immunoglobulin G solution (5% h-IgG manufactured by Benesis Corporation) with a physiological saline solution was filtered through the filter. The protein aqueous solution was filtered under a pressure of 0.294 MPa for three hours according to the dead-end method. After filtration, the filter was washed with 5 ml of a carbonate/bicarbonate buffer (pH 10), and then washed with 3 ml of water for injection. The diluted gold colloid solution prepared by the above method was then filtered through the washed filter. The filtration was carried out under a pressure of 0.098 MPa according to the dead-end method. The absorption at 529 nm was measured for the diluted gold colloid solution before filtration and 0.5 to 2.5 ml of filtrate fractions using a spectrophotometer ("UV-2450" manufactured by Shimadzu Corporation), and the logarithmic reduction value (LRV) of the gold particle was calculated. The absorbance was also measured in the same manner using a blank filter that was not subjected to h-IgG filtration and washing. As the results, the LRV of the filter that was subjected to the protein filtration and the washing was 1.30, and the LRV of the blank filter was 1.37. It was thus confirmed that the integrity of a hydrophilized synthetic polymer virus removal membrane through which a protein solution has been filtered can be accurately determined by utilizing the colloid solution according to the present invention.

Example 2

The same operations as in Example 1 were carried out, except that polyvinylpyrrolidone ("PVP K-15", average molecular weight: 10,000, manufactured by ISP) as a water-soluble polymer dispersant having a pyrrolidone group was used instead of the solution of Solsperse (registered trademark) 27000. The gold particles were sufficiently dispersed, and had an average particle diameter of 20.8 nm. As the results, the LRV of the filter that was subjected to protein filtration and washing was 1.76, and the LRV of the blank filter was 1.70. It was thus confirmed that the integrity of a hydrophilized synthetic polymer virus removal membrane through which a protein solution has been filtered can be accurately determined by utilizing the colloid solution according to the present invention.

Example 3

The same operations as in Example 1 were carried out, except that a filter (membrane area: 0.001 $m^2$) produced using a cuprammonium regenerated cellulose porous hollow fiber membrane (average pore size determined by the water flow method: 19.3 nm) produced using the method disclosed in Japanese Patent No. 3093821, was used instead of the filter produced using the porous virus removal hollow fiber membrane formed of hydrophilized polyvinylidene fluoride. The filtration pressure during the filtration of the protein aqueous solution by the dead-end method was 0.0784 MPa. As the results, the LRV of the filter that was subjected to protein filtration and washing was 1.57, and the LRV of the blank filter was 1.49. It was thus confirmed that the integrity of a cellulose virus removal membrane through which a protein solution has been filtered can be accurately determined by utilizing the colloid solution according to the present invention.

Example 4

The same operations as in Example 1 were carried out, except that polyoxyethylene polycyclic phenyl ether ("Newcol 610" manufactured by Nippon Nyukazai Co., Ltd.) as a nonionic surfactant having a polycyclic structure in a hydrophobic moiety was used instead of Solsperse (registered trademark) 27000.

As the results, the LRV of the filter that was subjected to protein filtration and washing was 1.77, and the LRV of the blank filter was 1.69. It was thus confirmed that the integrity of a hydrophilized synthetic polymer virus removal membrane through which a protein solution has been filtered can be accurately determined by utilizing the colloid solution according to the present invention.

Example 5

The same operations as in Example 1 were carried out, except that polyoxyethylene styryl phenyl ether ("Penerol SP 18" manufactured by Matsumoto Yushi-Seiyaku Co., Ltd.) as a nonionic surfactant having a polycyclic structure in a hydrophobic moiety was used instead of Solsperse (registered trademark) 27000. As the results, the LRV of the filter that was subjected to protein filtration and washing was 1.79, and the LRV of the blank filter was 1.70. It was thus confirmed that the integrity of a hydrophilized synthetic polymer virus removal membrane through which a protein solution has been filtered can be accurately determined by utilizing the colloid solution according to the present invention.

Example 6

The same operations as in Example 1 were carried out, except that polyoxyethylene sorbitan monolaurate ("Tween (registered trademark) 20" manufactured by Kishida Chemical Co., Ltd.) as a nonionic surfactant (polyoxyethylene sorbitan fatty acid ester) was used instead of Solsperse (registered trademark) 27000. As the results, the LRV of the filter that was subjected to protein filtration and washing was 1.72, and the LRV of the blank filter was 1.69. It was thus confirmed that the integrity of a hydrophilized synthetic polymer virus removal membrane through which a protein solution has been filtered can be accurately determined by utilizing the colloid solution according to the present invention.

Example 7

A reaction vessel was charged with 80 g of an aqueous solution of 14.7 mM chloroauric acid (special grade, manufactured by Wako Pure Chemical Industries, Ltd.). 320 g of distilled water and 18 g of a 4% sodium citrate aqueous solution were added to the solution, and the mixture was reacted at 76° C. for 30 minutes. After completion of the reaction, the mixture was cooled in a water bath for 15 minutes. After the addition of 6.7 g of polyoxyethylene β-naphthyl ether ("Solsperse (registered trademark) 27000" manufactured by Lubrizol Japan Ltd.) as a nonionic surfactant having a polycyclic structure in a hydrophobic moiety, 8.3 g of a 10% aqueous solution of poly(sodium 4-styrenesulfonate) (PSSA-Na, molecular weight: 70,000, manufactured by Sigma-Aldrich, Inc.) and further 3.6 g of a 30% aqueous solution of polyvinylpyrrolidone ("PVP K-15", average molecular weight: 10,000, manufactured by ISP) as a water-soluble polymer dispersant having a pyrrolidone group were added to the mixture to obtain a purple-red gold colloid solution. 10 g of the reaction solution was ten-fold diluted with an aqueous solution prepared by adding 1.6 g of a solution of Solsperse (registered trademark) 27000, 2.0 g of a 10% PSSA-Na (molecular weight: 70,000) solution, and 0.8 g of a 30% PVP solution to 95.6 g of water for injection to obtain. The same operations as in Example 1 were carried out, except that the red diluted gold colloid solution was used. The gold particles were sufficiently dispersed, and had an average particle diameter of 22.3 nm. As the results, the LRV of the filter that was subjected to protein filtration and washing was 1.44, and the LRV of the blank filter was 1.34. It was thus confirmed that the integrity of a hydrophilized synthetic polymer virus removal membrane through which a protein solution has been filtered can be accurately determined by utilizing the colloid solution according to the present invention.

Example 8

The same operations as in Example 7 were carried out, except that polyoxyethylene sorbitan monolaurate ("Tween (registered trademark) 20" manufactured by Kishida Chemical Co., Ltd.) as a nonionic surfactant (polyoxyethylene sorbitan fatty acid ester) was used instead of Solsperse (registered trademark) 27000. As the results, the LRV of the filter that was subjected to protein filtration and washing was 1.68, and the LRV of the blank filter was 1.65. It was thus confirmed that the integrity of a hydrophilized synthetic polymer virus removal membrane through which a protein solution has been filtered can be accurately determined by utilizing the colloid solution according to the present invention.

Example 9

The same operations as in Example 1 were carried out, except that a mixed solution of a 1% aqueous solution of polyoxyethylene β-naphthyl ether ("Solsperse (registered trademark) 27000" manufactured by Lubrizol Japan Ltd.) as a nonionic surfactant having a polycyclic structure in a hydrophobic moiety and a 1% aqueous solution of sodium hypochlorite, was used as the washing agent instead of the carbonate/bicarbonate buffer (pH 10). As the results, the LRV of the filter that was subjected to protein filtration and washing was 1.16, and the LRV of the blank filter was 1.08. It was thus confirmed that the integrity of a hydrophilized synthetic polymer virus removal membrane through which a protein solution has been filtered can be accurately determined by utilizing the colloid solution according to the present invention.

Example 10

A reaction vessel was charged with 15 g of an aqueous solution of 14.7 mM chloroauric acid (special grade, manufactured by Wako Pure Chemical Industries, Ltd.). 385 g of distilled water and 16 g of a 3% sodium citrate aqueous solution were added to the solution, the mixture was reacted for 60 minutes in a boiling state. After completion of the reaction, the mixture was cooled in a water bath for 15 minutes. After the addition of 6.7 g of polyoxyethylene β-naphthyl ether ("Solsperse (registered trademark) 27000" manufactured by Lubrizol Japan Ltd.) as a nonionic surfactant having a polycyclic structure in a hydrophobic moiety, 8.3 g of a 10% aqueous solution of poly(sodium 4-styrenesulfonate) (PSSA-Na, molecular weight: 70,000, manufactured by Sigma-Aldrich, Inc.) was added to the mixture to obtain a purple-red gold colloid solution. 45 g of the reaction solution was diluted with 55 ml of an aqueous solution prepared by adding 1.6 g of a solution of Solsperse (registered trademark) 27000 and 2.0 g of a 10% PSSA-Na (molecular weight: 70,000) aqueous solution to 96.4 g of water for injection to obtain a red diluted gold colloid solution. The absorption spectrum was measured using a spectrophotometer. The maximum absorption was observed at 525 nm (attributed to the plasmon absorption of gold). The gold colloid solution was dried on a mesh with a collodion membrane, and observed using a transmission electron microscope. The gold particles were sufficiently dispersed, and had an average particle diameter of 13.3 nm. A porous virus removal hollow fiber membrane (average pore size determined by the water flow method: 23.1 nm) formed of hydrophilized polyvinylidene fluoride (PVDF) was produced in the same manner as in Example 1, and a filter (membrane area: 0.001 m$^2$) was produced using the hollow fiber membrane. A protein aqueous solution prepared by diluting a human immunoglobulin G solution (5% h-IgG manufactured by Benesis Corporation) with a physiological saline solution was filtered through the filter. The protein aqueous solution was filtered under a pressure of 0.294 MPa for three hours according to the dead-end method. After filtration, the filter was washed with 5 ml of a carbonate/bicarbonate buffer (pH 10), and then washed with 3 ml of water for injection. The diluted gold colloid solution prepared by the above method was then filtered through the washed filter. The diluted gold colloid solution was filtered under a pressure of 0.196 MPa according to the dead-end method. The absorption at 525 nm was measured for the diluted gold colloid solution before filtration and 6.0 ml of a filtrate fraction using a spectrophotometer ("UV-2450" manufactured by Shimadzu Corporation), and the gold particle logarithmic reduction value (LRV) was calculated. The absorbance was also measured in the same manner using a blank filter that was not subjected to h-IgG filtration and washing. As the results, the LRV of the filter that was subjected to protein filtration and washing was 0.56, and the LRV of the blank filter was 0.52. It was thus confirmed that the integrity of a hydrophilized synthetic polymer virus removal membrane through which a protein solution has been filtered can be accurately determined by utilizing the colloid solution according to the present invention.

Example 11

A reaction vessel was charged with 80 g of an aqueous solution of 14.7 mM chloroauric acid (special grade, manufactured by Wako Pure Chemical Industries, Ltd.). 320 g of distilled water and 13.1 g of a 4% sodium citrate aqueous solution were added to the solution, and the mixture was reacted at 77° C. for 30 minutes. After completion of the reaction, the mixture was cooled in a water bath for 15 minutes. After the addition of 6.7 g of polyoxyethylene β-naphthyl ether ("Solsperse (registered trademark) 27000" manufactured by Lubrizol Japan Ltd.) as a nonionic surfactant having a polycyclic structure in a hydrophobic moiety, 8.3 g of a 10% aqueous solution of poly(sodium 4-styrenesulfonate) (PSSA-Na, molecular weight: 70,000, manufactured by Sigma-Aldrich, Inc.) as a anionic polymer having a sulfonic acid group was added to the mixture to obtain a purple gold colloid solution. 10 g of the reaction solution was ten-fold diluted with an aqueous solution prepared by adding 1.6 g of a solution of Solsperse (registered trademark) 27000 and 2.0 g of a 10% PSSA-Na (molecular weight: 70,000) aqueous solution to 96.4 g of water for injection to obtain a purple diluted gold colloid solution. The absorption spectrum was measured using a spectrophotometer. The maximum absorption was observed at 535 nm (attributed to the plasmon absorption of gold). The gold colloid solution was dried on a mesh with a collodion membrane, and observed using a transmission electron microscope. The gold particles were sufficiently dispersed, and had an average particle diameter of 35.0 nm. A virus removal porous hollow fiber membrane formed of hydrophilized polyvinylidene fluoride (PVDF) was produced in the same manner as in Example 1, except that the concentration of the polyvinylidene fluoride resin was changed to 38%. The average pore size determined by the water flow method of the hollow fiber membrane was 37.0 nm. A filtration was carried out in the same manner as in Example 1 using the membrane thus obtained. The filtration of filtering the protein aqueous solution was carried out according to the dead-end method, and the filtration pressure was 0.294 MPa. Also the filtration of filtering the diluted gold colloid solution was conducted by the dead-end method, and the filtration pressure was 0.078 MPa. The absorption at 535 nm was measured for the diluted gold colloid solution before filtration and 0.5 to 2.5 ml of filtrate fractions using a spectrophotometer ("UV-2450" manufactured by Shimadzu Corporation), and the gold particle logarithmic reduction value (LRV) was calculated. The absorbance was also measured in the same manner using a blank filter that was not subjected to h-IgG filtration and washing. As the results, the LRV of the filter that was subjected to protein filtration and washing was 2.05, and the LRV of the blank filter was 2.00. It was thus confirmed that the integrity of a hydrophilized synthetic polymer virus removal membrane through which a protein solution has been filtered can be accurately determined by utilizing the colloid solution according to the present invention.

Example 12

A reaction vessel was charged with 80 g of an aqueous solution of 14.7 mM chloroauric acid (special grade, manufactured by Wako Pure Chemical Industries, Ltd.). 320 g of distilled water and 6.4 g of a 4% sodium citrate aqueous solution were added to the solution, and the mixture was reacted at 84° C. for 30 minutes. After completion of the reaction, the mixture was cooled in a water bath for 15 minutes. After the addition of 6.7 g of polyoxyethylene β-naphthyl ether ("Solsperse (registered trademark) 27000" manufactured by Lubrizol Japan Ltd.) as a nonionic surfactant having a polycyclic structure in a hydrophobic moiety), 8.3 g of a 10% aqueous solution of poly(sodium 4-styrenesulfonate) (PSSA-Na, molecular weight: 70,000, manufactured by Sigma-Aldrich, Inc.) as a anionic polymer having a sulfonic acid group was added to the mixture to obtain a purple gold colloid solution. 10 g of the reaction solution was ten-fold diluted with an aqueous solution prepared by adding 1.6 g of a solution of Solsperse (registered trademark) 27000 and 2.0 g of a 10% PSSA-Na (molecular weight: 70,000) aqueous solution to 96.4 g of water for injection to obtain a purple diluted gold colloid solution. The absorption spectrum was measured using a spectrophotometer. The maximum absorption was observed at 541 nm (attributed to plasmon absorption of gold). The gold colloid solution was dried on a mesh with a collodion membrane, and observed using a transmission electron microscope. The gold particles were sufficiently dispersed, and had an average particle diameter of 44.9 nm. A virus removal porous hollow fiber membrane formed of hydrophilized polyvinylidene fluoride (PVDF) was produced in the same manner as in Example 1, except that the concentration of the polyvinylidene fluoride resin was changed to 30%. The average pore size determined by the water flow method of the hollow fiber membrane was 47.0 nm. A filtration was carried out in the same manner as in Example 1 using the membrane thus obtained. The filtration of filtering a protein aqueous solution was carried out according to the dead-end method, and the filtration pressure was 0.294 MPa. Also the filtration of filtering the diluted gold colloid solution was conducted by the dead-end method, and the filtration pressure was 0.078 MPa. The absorption at 540 nm was measured for the diluted gold colloid solution before filtration and 0.5 to 2.5 ml of filtrate fractions using a spectrophotometer ("UV-2450" manufactured by Shimadzu Corporation), and the gold particle logarithmic reduction value (LRV) was calculated. The absorbance was also measured in the same manner using a blank filter that was not subjected to h-IgG filtration and washing. As the results, the LRV of the filter that was subjected to protein filtration and washing was 2.00, and the LRV of the blank filter was 2.10. It was thus confirmed that the integrity of even a hydrophilized synthetic polymer membrane through which a protein solution has been filtered can be accurately determined by utilizing the colloid solution according to the present invention.

Comparative Example 1

A reaction vessel was charged with 80 g of an aqueous solution of 14.7 mM chloroauric acid (special grade, manufactured by Wako Pure Chemical Industries, Ltd.). 320 g of distilled water and 18 g of a 4% sodium citrate aqueous solution were added to the solution, and the mixture was reacted at 76° C. for 30 minutes. After completion of the reaction, the mixture was cooled in a water bath for 15 minutes. 6.7 g of polyoxyethylene β-naphthyl ether ("Solsperse (registered trademark) 27000" manufactured by Lubrizol Japan Ltd.) as a nonionic surfactant having a polycyclic structure in a hydrophobic moiety was then added to the mixture to obtain a purple-red gold colloid solution. 10 g of the reaction solution was ten-fold diluted with an aqueous solution prepared by adding 1.6 g of a solution of Solsperse (registered trademark) 27000 to 98.4 g of water for injection to obtain a red diluted gold colloid solution. The same operations as in Example 1 were carried out, except that the red diluted gold colloid solution was used. The gold particles were sufficiently dispersed, and had an average particle diameter of 22.3 nm.

As the result, the LRV of the filter was 3.0 or more, that is equal to or less than the detection limit, and the colloid adhered to the membrane so that an accurate measurement could not be performed.

Comparative Example 2

A filtration was performed using a PVDF porous hollow fiber membrane produced in the same manner as in Example 2, except for using a diluted gold colloid solution to which poly(sodium 4-styrenesulfonate) (PSSA-Na, molecular weight: 70,000, manufactured by Sigma-Aldrich, Inc.) as an anionic polymer having a sulfonic acid group was not added, and the gold colloid logarithmic reduction value (LRV) was calculated. The gold particles were sufficiently dispersed, and had an average particle diameter of 22.3 nm. As the result, the LRV of the filter was 3.0 or more, that is, equal to or less than the detection limit, and the colloid adhered to the membrane so that an accurate measurement could not be performed.

Comparative Example 3

A filtration was performed using a PVDF porous hollow fiber membrane produced in the same manner as in Example 4, except for using a diluted gold colloid solution to which poly(sodium 4-styrenesulfonate) (PSSA-Na, molecular weight: 70,000, manufactured by Sigma-Aldrich, Inc.) as an anionic polymer having a sulfonic acid group was not added, and the gold colloid logarithmic reduction value (LRV) was calculated. The gold particles were sufficiently dispersed, and had an average particle diameter of 20.8 nm. As the result, the LRV of the filter was 3.0 or more, that is, equal to or less than the detection limit, and the colloid adhered to the membrane so that an accurate measurement could not be performed.

Comparative Example 4

A filtration was performed using a PVDF porous hollow fiber membrane produced in the same manner as in Example 6, except for using a diluted gold colloid solution to which poly(sodium 4-styrenesulfonate) (PSSA-Na, molecular weight: 70,000, manufactured by Sigma-Aldrich, Inc.) as an anionic polymer having a sulfonic acid group was not added, and the gold colloid logarithmic reduction value (LRV) was calculated. The gold particles were sufficiently dispersed, and had an average particle diameter of 22.3 nm. As the result, the LRV of the filter was 3.0 or more, that is, equal to or less than the detection limit, and the colloid adhered to the membrane so that an accurate measurement could not be performed.

Comparative Example 5

A filtration was performed using a PVDF porous hollow fiber membrane produced in the same manner as in Example 7, except for using a diluted gold colloid solution to which poly(sodium 4-styrenesulfonate) (PSSA-Na, molecular weight: 70,000, manufactured by Sigma-Aldrich, Inc.) as an anionic polymer having a sulfonic acid group was not added, and the gold colloid logarithmic reduction value (LRV) was calculated. The gold particles were sufficiently dispersed, and had an average particle diameter of 22.3 nm. As the result, the LRV of the filter was 3.0 or more, that is, equal to or less than the detection limit, and the colloid adhered to the membrane so that an accurate measurement could not be performed.

Comparative Example 6

A filtration was performed using a PVDF porous hollow fiber membrane produced in the same manner as in Example 2, except for using a red diluted gold colloid solution to which 0.27% of sodium lauryl sulfate (manufactured by Nacalai Tesque, Inc.) was added instead of poly(sodium 4-styrenesulfonate) (PSSA-Na, molecular weight: 70,000, manufactured by Sigma-Aldrich, Inc.) as an anionic polymer having a sulfonic acid group, and the gold colloid logarithmic reduction value (LRV) was calculated. The gold particles were sufficiently dispersed, and had an average particle diameter of 20.8 nm. As the result, the LRV of the filter was 3.0 or more, that is, equal to or less than the detection limit, and the colloid adhered to the membrane so that an accurate measurement could not be performed.

Comparative Example 7

A filtration was performed using a PVDF porous hollow fiber membrane produced in the same manner as in Example 1, except for using a red diluted gold colloid solution to which a 30% aqueous solution of sodium polyacrylate ("PAA-Na", molecular weight: 5000 to 6000, manufactured by Nihon Junyaku Co., Ltd.) was added instead of poly(sodium 4-styrenesulfonate) (PSSA-Na, molecular weight: 70,000, manufactured by Sigma-Aldrich, Inc.) as an anionic polymer having a sulfonic acid group, and the gold colloid logarithmic reduction value (LRV) was calculated. As the result, the LRV of the filter that was subjected to protein filtration and washing was 2.25, and the LRV of the blank filter was 1.82. Since the LRV increased due to the protein filtration and washing operations, the integrity of the filter could not be accurately examined.

Comparative Example 8

A filtration was performed using a PVDF porous hollow fiber membrane produced in the same manner as in Example 2, except for using a red diluted gold colloid solution to which a 30% aqueous solution of sodium polyacrylate ("PAA-Na", molecular weight: 5000 to 6000, manufactured by Nihon Junyaku Co., Ltd.) was added instead of poly(sodium 4-styrenesulfonate) (PSSA-Na, molecular weight: 70,000, manufactured by Sigma-Aldrich, Inc.) as an anionic polymer having a sulfonic acid group, and the gold colloid logarithmic reduction value (LRV) was calculated. As the result, the LRV of the filter that was subjected to protein filtration and washing was 2.21, and the LRV of the blank filter was 1.95. Since the LRV increased due to the protein filtration and washing operations, the integrity of the filter could not be accurately examined.

Comparative Example 9

A filtration was performed using a cuprammonium regenerated cellulose porous hollow fiber membrane produced in the same manner as in Example 3, except for using a red diluted gold colloid solution to which a 30% aqueous solution of sodium polyacrylate ("PAA-Na", molecular weight: 5000 to 6000, manufactured by Nihon Junyaku Co., Ltd.) was added instead of poly(sodium 4-styrenesulfonate) (PSSA-Na, molecular weight: 70,000, manufactured by Sigma-Aldrich, Inc.) as an anionic polymer having a sulfonic acid group), and the gold colloid logarithmic reduction value (LRV) was calculated. As the result, the LRV of the filter that was subjected to protein filtration and washing was 1.91, and the LRV of the blank filter was 1.60. Since the LRV increased due to the protein filtration and washing operations, the integrity of the filter could not be accurately examined.

Comparative Example 10

A filtration was performed using a PVDF porous hollow fiber membrane produced in the same manner as in Example 1, except for using a red diluted gold colloid solution to which polyoxyethylene ($C_9$) alkyl phenyl ether ("Nonipol (registered trademark) 120" manufactured by Matsumoto Yushi-Seiyaku Co., Ltd.) was added instead of polyoxyethylene β-naphthyl ether ("Solsperse (registered trademark) 27000" manufactured by Lubrizol Japan Ltd.) as the nonionic surfactant having a polycyclic structure in a hydrophobic moiety, and the gold colloid logarithmic reduction value (LRV) was calculated. As the result, the LRV of the filter that was subjected to protein filtration and washing was 2.16, and the LRV of the blank filter was 1.92. Since the LRV increased due to the protein filtration and washing operations, the integrity of the filter could not be accurately examined.

Comparative Example 11

A filtration was performed using a PVDF porous hollow fiber membrane produced in the same manner as in Example 1, except for using a red diluted gold colloid solution to which polyoxyethylene oleyl ether (manufactured by Wako Pure Chemical Industries, Ltd.) was added instead of polyoxyethylene β-naphthyl ether ("Solsperse (registered trademark) 27000" manufactured by Lubrizol Japan Ltd.) as the nonionic surfactant having a polycyclic structure in a hydrophobic moiety, and the gold colloid logarithmic reduction value (LRV) was calculated. As the result, the LRV of the filter that was subjected to protein filtration and washing was 2.08, and the LRV of the blank filter was 1.82. Since the LRV increased due to the protein filtration and washing operations, the integrity of the filter could not be accurately determined.

Comparative Example 12

A reaction vessel was charged with 15 g of an aqueous solution of 14.7 mM chloroauric acid (special grade, manufactured by Wako Pure Chemical Industries, Ltd.). 385 g of distilled water and 20 g of a 3% sodium citrate aqueous solution, the mixture was reacted for 60 minutes in a boiling state. After completion of the reaction, the subsequent operations were proceeded in the same manner as in Example 1, except that the mixture was cooled in a water bath for 15 minutes. A gold colloid solution having an average particle diameter of less than 5 nm could not be produced even though the 3% sodium citrate aqueous solution was added 20 g or more.

Comparative Example 13

A reaction vessel was charged with 80 g of an aqueous solution of 14.7 mM chloroauric acid (special grade, manufactured by Wako Pure Chemical Industries, Ltd.). 320 g of distilled water and 3.0 g of a 4% sodium citrate aqueous solution were added to the solution, the mixture was reacted at 90° C. for 30 minutes. After completion of the reaction, the subsequent operations were proceeded in the same manner as in Example 1, except that the mixture was cooled in a water bath for 15 minutes. The average particle diameter of the resulting gold colloid solution was 55 nm or more. However, the gold colloid solution was brown, aggregation and precipitation occurred immediately, and a gold colloid solution having a uniform particle diameter could not be obtained.

The results obtained by the examples and comparative examples are summarized in Table 1.

TABLE 1

| | Material of porous membrane | Anionic polymer having sulfonic acid group | Nonionic surfactant | Water-soluble polymer having pyrrolidone group | Washing slution | Protein filtration | LRV | Difference in LRV |
|---|---|---|---|---|---|---|---|---|
| Example 1 | Hydrophilized PVDF hollow fiber membrane | PSSA-Na | Solsperse (registered trademark) 27000 | — | Carbonate/ bicarbonate buffer (pH 10) | None | 1.37 | 0.07 |
| | | | | | | Done | 1.30 | |
| Example 2 | Hydrophilized PVDF hollow fiber membrane | PSSA-Na | — | PVP | | None | 1.70 | −0.06 |
| | | | | | | Done | 1.76 | |
| Example 3 | Regenerated cellulose hollow fiber membrane | PSSA-Na | Solsperse (registered trademark) 27000 | — | | None | 1.49 | −0.08 |
| | | | | | | Done | 1.57 | |
| Example 4 | Hydrophilized PVDF hollow fiber membrane | PSSA-Na | Newcol 610 | — | | None | 1.69 | −0.08 |
| | | | | | | Done | 1.77 | |
| Example 5 | Hydrophilized PVDF hollow fiber membrane | PSSA-Na | Penerol SP18 | — | Carbonate/ bicarbonate buffer (pH 10) | None | 1.70 | −0.09 |
| | | | | | | Done | 1.79 | |
| Example 6 | Hydrophilized PVDF hollow fiber membrane | PSSA-Na | Tween (registered trademark) 20 | — | | None | 1.69 | −0.03 |
| | | | | | | Done | 1.72 | |
| Example 7 | Hydrophilized PVDF hollow fiber membrane | PSSA-Na | Solsperse (registered trademark) 27000 | PVP | | None | 1.34 | −0.10 |
| | | | | | | Done | 1.44 | |
| Example 8 | Hydrophilized PVDF hollow fiber membrane | PSSA-Na | Tween (registered trademark) 20 | PVP | | None | 1.65 | −0.03 |
| | | | | | | Done | 1.68 | |
| Example 9 | Hydrophilized PVDF hollow fiber membrane | PSSA-Na | Solsperse (registered trademark) 27000 | — | Solsperse (registered trademark) 27000 + sodium hypochloride | None | 1.08 | −0.08 |
| | | | | | | Done | 1.16 | |

TABLE 1-continued

| | Material of porous membrane | Anionic polymer having sulfonic acid group | Surfactant | Water-soluble polymer | Washing solution | Protein filtration | LRV | Difference in LRV |
|---|---|---|---|---|---|---|---|---|
| Comparative Example 1 | Hydrophilized PVDF hollow fiber membrane | — | Solsperse (registered trademark) 27000 | — | Carbonate/bicarbonate buffer (pH 10) | None | >3.00 | |
| Comparative Example 2 | Hydrophilized PVDF hollow fiber membrane | — | — | PVP | | None | >3.00 | |
| Comparative Example 3 | Hydrophilized PVDF hollow fiber membrane | — | Newcol 610 | — | | None | >3.00 | |
| Comparative Example 4 | Hydrophilized PVDF hollow fiber membrane | — | Tween (registered trademark) 20 | — | | None | >3.00 | |
| Comparative Example 5 | Hydrophilized PVDF hollow fiber membrane | — | Solsperse (registered trademark) 27000 | PVP | | None | >3.00 | |
| Comparative Example 6 | Hydrophilized PVDF hollow fiber membrane | — | SDS | PVP | | None | >3.00 | |
| Comparative Example 7 | Hydrophilized PVDF hollow fiber membrane | — | Solsperse (registered trademark) 27000 | PAA-Na | | None / Done | 1.82 / 2.25 | −0.43 |
| Comparative Example 8 | Hydrophilized PVDF hollow fiber membrane | — | — | PAA-Na, PVP | | None / Done | 1.95 / 2.21 | −0.26 |
| Comparative Example 9 | Regenerated cellulose hollow fiber membrane | — | Solsperse (registered trademark) 27000 | PAA-Na | | None / Done | 1.60 / 1.91 | −0.31 |
| Comparative Example 10 | Hydrophilized PVDF hollow fiber membrane | PSSA-Na | Nonipol (registered trademark) 120 | — | | None / Done | 1.92 / 2.16 | −0.24 |
| Comparative Example 11 | Hydrophilized PVDF hollow fiber membrane | PSSA-Na | Polyoxyethylene oleyl ether | — | | None / Done | 1.82 / 2.08 | −0.26 |

| | Material of porous membrane | Anionic polymer having sulfonic acid group | Nonionic surfactant | Average particle diameter (nm) | Washing solution | Protein filtration | LRV | Difference in LRV |
|---|---|---|---|---|---|---|---|---|
| Example 1 | Hydrophilized PVDF hollow fiber membrane | PSSA-Na | Solsperse (registered trademark) 27000 | 22.3 | Carbonate/bicarbonate buffer (pH 10) | None / Done | 1.37 / 1.30 | 0.07 |
| Example 10 | | | | 13.3 | | None / Done | 0.56 / 0.52 | 0.04 |
| Example 11 | | | | 35.0 | | None / Done | 2.05 / 2.00 | 0.05 |
| Example 12 | | | | 44.9 | | None / Done | 2.00 / 2.10 | 0.10 |
| Comparative Example 12 | | PSSA-Na | Solsperse (registered trademark) 27000 | <5 | | Could not be produced | | |
| Comparative Example 13 | | PSSA-Na | Solsperse (registered trademark) 27000 | >55 | | Aggregation and precipitation occurred | | |

INDUSTRIAL APPLICABILITY

The integrity test method using the colloid solution containing metal particles according to the present invention is suitable as a practical integrity test for a microporous membrane after the microporous membrane has been used as a virus removal membrane.

What is claimed is:

1. A method of testing the integrity of a microporous membrane comprising filtering a colloid solution through the microporous membrane which is a synthetic polymer virus removal membrane, the colloid solution comprising a solvent and metal particles dispersed in the solvent, and the solvent comprising components (A) and (B), (A) and (C), or (A), (B) and (C), wherein
 the component (A) is an anionic polymer having a sulfonic acid group, the polymer comprising polystyrene sulfonate,
 the component (B) is at least one nonionic surfactant selected from the group consisting of a nonionic surfactant having a polycyclic structure in a hydrophobic moiety and a polyoxyethylene sorbitan fatty acid ester, and
 the component (C) is a water-soluble polymer having a pyrrolidone group.

2. The method according to claim 1, wherein the synthetic polymer virus removal membrane is a hydrophilized thermoplastic polymer membrane.

3. The method according to claim 2, wherein the thermoplastic polymer of the hydrophilized thermoplastic polymer membrane is selected from the group consisting of polyvinylidene fluoride, polyethersulfone, and polysulfone.

4. The method according to claim 1, wherein the metal of the metal particles is selected from the group consisting of gold, silver, platinum, rhodium, palladium, ruthenium, iridium, osmium, iron, and copper.

5. The method according to claim 4, wherein the metal particles have an average particle diameter of 10 to 50 nm.

6. The method according to claim 5, wherein the coefficient of variation of the average particle diameter of the metal particles is 27% or less.

7. The method according to claim 1, wherein the nonionic surfactant having a polycyclic structure in a hydrophobic moiety is at least one compound selected from the group consisting of a polyoxyethylene polycyclic phenyl ether, polyoxyethylene β-naphthyl ether, and polyoxyethylene styryl phenyl ether.

8. The method according to claim 1, wherein the polyoxyethylene sorbitan fatty acid ester is polyoxyethylene sorbitan monolaurate and/or polyoxyethylene sorbitan monooleate.

9. The method according to claim 1, wherein the water-soluble polymer having a pyrrolidone group is polyvinylpyrrolidone or a polyvinylpyrrolidone/styrene copolymer.

10. The method according to claim 1, wherein the virus removal membrane has been subjected to filtration with a protein solution.

11. The method according to claim 1, wherein the virus removal membrane is a membrane which has been washed with a mixed solution that contains a nonionic surfactant having a polycyclic structure in a hydrophobic moiety and sodium hypochlorite after filtrating a protein solution.

12. The method according to claim 1, wherein the metal colloid solution is obtained by dissolving the component (B) and/or the component (C) in a solution prepared by dissolving a metal compound in a solvent to precipitate metal particles, then further dissolving the component (A) in the solution.

13. The method according to claim 1, wherein the difference in the logarithmic reduction value (LRV) of the metal particles measured before and after filtrating a protein solution is 0.1 or less.

14. The method according to claim 1, wherein the virus removal membrane is a membrane which has been washed with a basic buffer after filtrating a protein solution.

15. The method according to claim 14, wherein the basic buffer is selected from the group consisting of a carbonate, a bicarbonate, a borate, and a phosphate.

16. The method according to claim 1, wherein the anionic polymer having a sulfonic acid group has a molecular weight of $1 \times 10^3$ to $2 \times 10^6$.

17. The method according to claim 1, wherein the content of the anionic polymer having a sulfonic acid group in the colloid solution is 0.01 to 20 wt %.

18. The method according to claim 1, wherein proteins are present in the virus removal membrane.

* * * * *